United States Patent [19]

Gogol

[11] Patent Number: 4,692,630

[45] Date of Patent: Sep. 8, 1987

[54] WAVELENGTH SPECIFIC DETECTION SYSTEM FOR MEASURING THE PARTIAL PRESSURE OF A GAS EXCITED BY AN ELECTRON BEAM

[75] Inventor: Carl A. Gogol, Cazenovia, N.Y.

[73] Assignee: Inficon Leybold-Heraeus, E. Syracuse, N.Y.

[21] Appl. No.: 867,093

[22] Filed: May 27, 1986

[51] Int. Cl.[4] .............................................. H01J 27/00
[52] U.S. Cl. ................................. 250/573; 250/423 P
[58] Field of Search ................... 250/573, 423 P, 292; 73/705, 754

[56] References Cited

U.S. PATENT DOCUMENTS

| | | | |
|---|---|---|---|
| 4,170,736 | 10/1979 | Wessel | 250/423 P |
| 4,362,936 | 12/1982 | Hofmann et al. | 250/292 |
| 4,413,185 | 11/1983 | Leveson et al. | 250/423 P |

Primary Examiner—David C. Nelms
Assistant Examiner—William L. Oen
Attorney, Agent, or Firm—Bruns and Wall

[57] ABSTRACT

An optical partial pressure gas analyzer employs an electron beam to excite the outer electrons of gas atoms or molecules, and one or more photomultiplier tubes or other similar detectors to detect wavelengths of photons characteristic of the decay of the outer electrons of one or more species of gas molecules. The photomultiplier tubes have a viewing direction substantially at right angles to the electron beam. A Faraday trap or similar device is employed to avoid secondary electron generation. Thin-film interference filters are favorably employed to pass a specific characteristic wavelength of the desired species, and to reject other wavelengths. An electromechanical filter changer permits each photomultiplier tube to analyze two or more gasses alternately.

11 Claims, 3 Drawing Figures

WAVELENGTH SPECIFIC DETECTION SYSTEM FOR MEASURING THE PARTIAL PRESSURE OF A GAS EXCITED BY AN ELECTRON BEAM

BACKGROUND OF THE INVENTION

This invention relates to residual gas analyzers, and is more particularly directed to a partial pressure gas analyzer for measuring the partial pressures of gasses in a vacuum process chamber. The invention pertains more specifically to a partial pressure controller for measuring the partial pressures of chamber gasses during a sputtering deposition process.

Numerous types of devices have been proposed for measuring the total pressure or quantity of a gas or gasses in a vessel, yet only a small number of devices have been proposed for sensing the type and partial pressure of each gas within the vessel. The prevalent type of sensor used is a quadrupole-type mass spectrometer, a typical one of which is described in U.S. Pat No. 4,362,936. In these analyzers, the gasses are ionized and then separated in a quadrupole mass analyzer. These analyzers operate on the principle that the ions of various gas species have a unique charge to mass ratio signature. Various other types of mass spectrometers include magnetic-sector and time-of-flight devices. Other sensors, less commonly used in the art, depend on the separation of species by the frequency of oscillation of ions or by the size of the orbit of a gas ion in an applied RF field.

In general, all these types of analyzers depend on ionization and subsequent charge-to-mass filtering, and require relatively high vacuum ($10^{-5}$ Torr or better) to achieve good separation. At high pressures, the collisional scattering between ions of the same or different charge-to-mass ratio, as well as collisions induced by neutral atoms, makes the identification of specific species and measurement of their quantity extremely difficult. The conventional approach to solving this problem is to employ a pressure reduction stage that restricts the amount of gas permitted to enter the ionizer, and a separate high vacuum pump that pumps out a large fraction of the gas that enters the ionizer. This additional apparatus adds a time delay to the control of the process gasses, and in addition substantially doubles the cost of measurement. These mass analysis systems are typically burdened with high maintenance costs and require frequent calibration to ensure accuracy.

Other methods of gas analysis, such as infrared line absorption, do not work well at the reduced gas pressures used in a typical vacuum deposition or sputtering process, in which the pressure is typically on the order of $10^{-6}$ atmospheres.

Electron beam excitation has previously been employed only to measure deposition rates of evaporant particles, as discussed in U.S. Pat. No. 4,036,167. For a number of reasons, that structure was inappropriate to analyze background gasses at sputtering pressures.

OBJECTS AND SUMMARY OF THE INVENTION

Accordingly, it is an object of this invention to provide partial pressure gas analysis apparatus operative for high and midrange vacuum processing.

It is a more specific object of this invention to provide apparatus for measuring the composition of gasses over a wide range of compositions up to total pressures on the order of $200 \times 10^{31}$ 3 Torr, without requiring a pressure reduction stage.

It is another object of this invention to provide partial pressure gas measurement apparatus that avoids time delay between a change in partial pressure of a gaseous species and its detection.

In accordance with an aspect of the invention a sensor measures the amount of a specific gas within a vacuum process chamber. An electron beam is generated with sufficient energy to excite the outer shell electrons of the atoms and molecules of the gas in question. The electrons excited by the beam decay back to a lower energy state and emit photons of a wavelength characteristic of the specific gas. A photodetector is placed with its viewing direction normal to the path of the electron beam, and includes a filter or other discriminating means for passing the specific wavelength photons for the gas in question. The photodetector produces a proportional electrical output current that is linearly related to the partial pressure of the specific gas. Interchangeable thin-filter interference filters can be used as the discriminating means, and a photomultiplier tube can serve as the photodetector. Two or more filter and photomultiplier tube arrangements, in combination with the electron beam generating element, can be employed to measure partial pressure of two or more process gasses.

The above and many other objects, features, and advantages of the invention will be more fully understood from the ensuing detailed description of the preferred embodiment, which is to be read in connection with the accompanying drawing.

DETAILED DESCRIPTION OF THE PREFERRED EMBODIMENT

Figure 3:
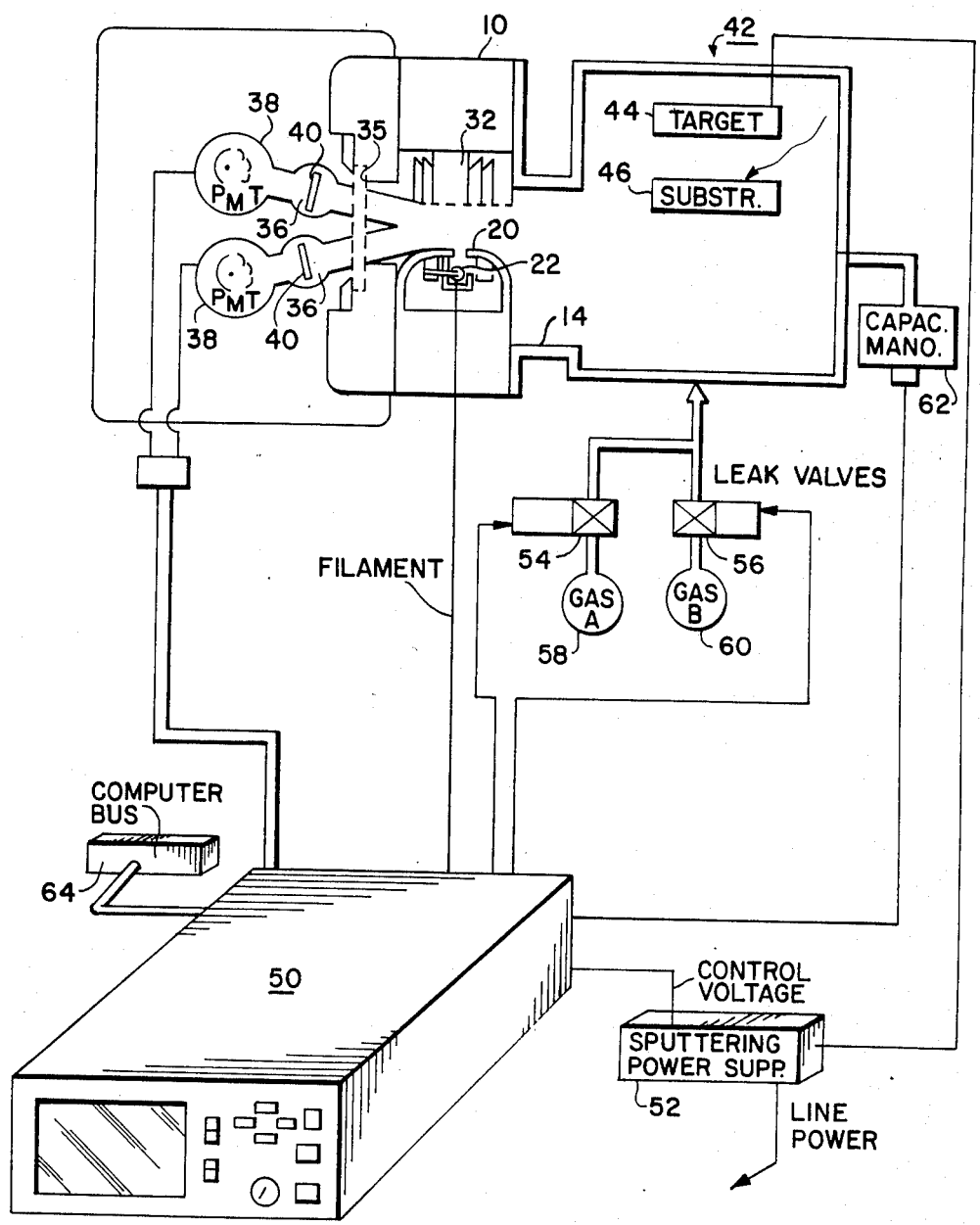
FIG. 3 is a general schematic view of a sputtering process arrangement, including a partial pressure controller employing the sensor of FIGS. 1 and 2.

With reference to the drawing, and initially to FIG. 3 thereof, a partial pressure gas analyzer assembly 10 is formed of a shell or housing 12 having a neck 14 in communication with a sputtering or vacuum deposition chamber (not shown in this view). The housing has an electron gun case portion 16 to which the neck 14 is connected, and a photodetector case portion 18 thereabove. An electron gun or electron beam generating device 20 is situated in the gun case portion 16. This electron gun 20 is a frame 22 on which is stretched a filament 24 which is heated for emission of electrons. Ends of the filament 24 are connected to external leads, not shown. An apertured plate 26 has an opening 30 that is elongated in the horizontal direction to admit beams of electrons in one horizontal direction and spread out somewhat in the horizontal plane. It is preferred not to employ focussing electrodes for the electron beam, as that would increase the path of the electrons through the gasses. By keeping this path as short as possible, the present invention avoids optical non-linearities due to uncontrolled excitations from detached electrons from the ionized atoms and molecules. Glow discharge breakdown is also avoided by minimizing these geometric distances. A Faraday trap 32 or other similar device is disposed within the electron gun case portion 16 to trap the generated electron beam so as to avoid and minimize secondary electron emission.

Figure 1:
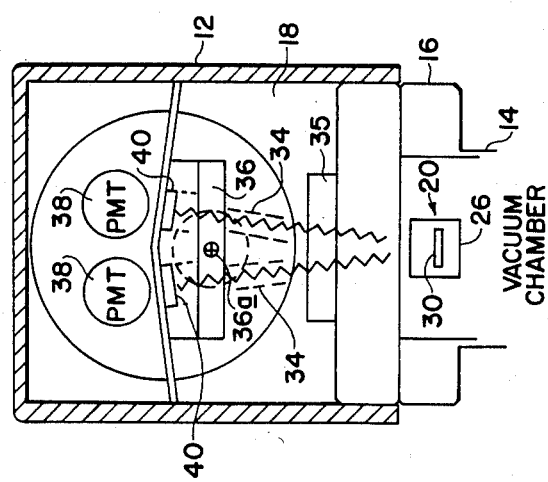
FIG. 1 is a front sectional view of a sensor according to an embodiment of this invention.

A pair of viewing paths 34 are defined within the photodetector case portion 18 of the housing 12 to view the space between the plate 26 and the Faraday trap 32. The photons that are released by the de-excitation of atoms and molecules of the gas are passed along the viewing paths 34 through a window 35 that also function as a portion of the enclosure of the case portion 18 for containing the gas. Window 35 is highly transparent to photons in the wavelengths of interest. These viewing paths (to the left and right in FIG. 1) lead through a filter holder 36 to respective photomultiplier tubes 38 or other suitable photosensors. The viewing paths 34 each have filters 40 disposed across them in advance of the associated photomultiplier tube 38. The output current of the photomultiplier tube 38 is generally proportional to the partial pressure of the gas being observed. Solid-state light-to- electric current converting devices are well known, and could be substituted for the photomultiplier tubes 38.

The filter holder 36 preferably contains a set of removable and replaceable thin-film interference filters 40a, 40b which pass only a selected wavelength that identifies uniquely the molecules of the gas being analyzed, and rejects other wavelengths. Photons emitted from two different species may be very close to one another in wavelength, and some difficulty in distinguishing between two different gasses can be encountered at a given wavelength. However, there are normally several useable spectral emission lines for each given species of gas. Accordingly, the filters are selected not only on the basis of maximum signal strength, but also for limiting interference from emissions of other gasses. The wavelengths used for monitoring gas partial pressures are chosen also on the basis of the amount of optical signal generated from the gas relative to black body radiation that may be present due to the hot cathode filament as well as to maximize the separation of wavelengths from other emission wavelengths in the mixture of gasses being analyzed.

The geometry here shields the photomultiplier tubes 38 from being on a direct line of sight with the electron gun filament cathode 24, so that little if any stray black body radiation will reach the photomultiplier tubes 38. As an alternative, a cold-cathode electron discharge element could be substituted for the electron gun 20. These devices are well known, and need not be specifically shown or discussed.

The preferable filter for this device is, as aforesaid, the thin-film interference filter, which is inexpensive, requires no adjustment, and is generally efficient in the transmission of photons of a given desired wavelength. Diffraction gratings can also be employed as the filter 40. It is also possible to use a monochromator or other more complex optical wavelength separation scheme.

In this embodiment, an electromechanical filter exchanger is formed of a motor 41 which rotates a threaded shaft 36a of the filter holder 36. This moves the latter translationally (left to right in FIG. 2) to substitute one set of filters 40a for another set 40b. The exchange of filters 40a, 40b effected by the filter holder 36, permits a number of gasses to be analyzed alternately. In this way, each photosensor 38 can be employed for analysis of more than one gaseous species.

The voltages for the filament 24 are selected to energize the gas molecules' orbital electrons on the order of a fraction of an electron volt to several electron volts. Voltages of 100 V. or below have been found satisfactory for the electron beam generating element. Maintaining voltages at this level prevents the sensor structures from sustaining spontaneous glow discharge at the pressures of interest. The collisional interaction of electron beam with the outer electrons of the gas molecules and atoms results in a transfer of energy to the latter. These molecules and atoms are excited and emit photons at a characteristic wavelength before returning to their original state.

It is generally preferred that the beam of electrons be modulated or chopped. This provides a simple means for discriminating between photons from the de-excitation of the gas atoms and photons of simlar wavelength which may be simply background or filament light. This procedure is known as phase-sensitive detection. A modulation frequency of about 500 Hz is useful.

As implemented, the neck 14 of the assembly 10 is connected to a part of the vacuum chamber that is close to the main chamber volume, but not in the way of any processing equipment. The neck 14 defines a port which is in communication with the main chamber volume, and passes a representative sample of the chamber gas. This construction minimizes any delays in transport in any fractions of the gas mixture, so time delays due to diffusion are kept to a minimum.

Light that is produced by electron beam excitation of the gas is viewed in a direction generally orthogonal to the direction of the electron beam. This geometry minimizes the amount of black-body radiation from the incandescence of the hot filament 24 that reaches the photomultiplier tube 38. Another benefit of the geometry of this arrangement is that the distance from the excitation of the gas to the detector is minimized. Because of the nature of the excitation process, the resultant photon flux is nearly isotropic in directionality. Photon collection efficiency is related to the inverse of the distance squared, so a maximum of photon collection is effected by placing the viewing paths 34 as close to the beam-excited gas as possible.

It has also been discovered by the inventor herein that the functional relationship between pressure of the gas and the collected photon flux is significantly affected by changes in the distance of photon travel through the gasses. With the sensor designed to keep this distance at a minimum, it was discovered that the relationship was rather more linear than the relationship exhibited when a longer photon path through the gas is employed. This is believed to be due to the phenomenon of self absorption. Photons produced by electron beam excitation are very narrowly specific in wavelength, and those same wavelengths are very likely to be reabsorbed by a molecule of the gas of the same species as the molecule that emitted those wavelengths. Therefore, there is a dramatic reduction in intensity at higher pressures as compared with the level predicted by lower pressure values, if the photon must traverse a significant thickness of the gas. Of course, it is desirable to have the response as nearly linear as possible to simplify the computation that is required. Accordingly, the distance through the gas that the excitation photons must travel should be kept to the minimum.

As aforementioned, each single species of gas will produce many distinct wavelengths or frequencies. Two different species of gas may emit photons which are very close to one another in wavelength. If this presents a problem in separation of the two species at a given wavelength, a different wavelength generally exists for each species which has an adequate separation from any wavelength of the other species. Thus, wavelengths are selected for monitoring not only based on intensity at that wavelength, but also based on separation from any likely wavelength of other gasses that are present, and on the absence of black body radiation or other background noise in the general wavelength region. The wavelengths thus chosen are thus a compromise that may vary with a specific mixture of gasses anticipated, and with the ability of the filtering means used to pass the wavelengths of interest and reject others.

Preferably, thin-film interference filters are employed as the filters 40. Their low space requirement allows the advantage of employing an electro mechanical automatic filter changer within the filter holder 36. This permits the same photosensor 38 to analyze partial pressures of several gasses alternately.

Figure 2:
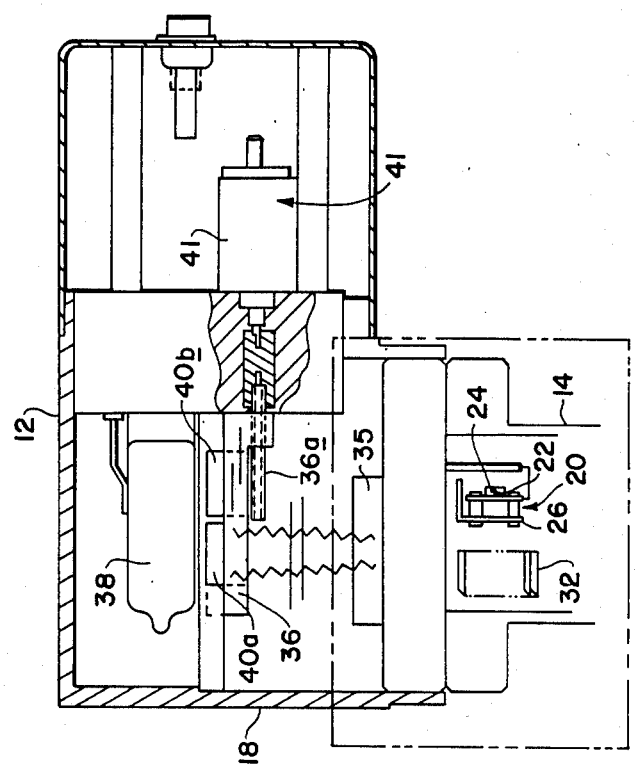
FIG. 2 is a side sectional elevation of the sensor of FIG. 1.

A measurement and control system employing the above-described sensor assembly for two gasses is shown in FIG. 2. This system has not only the abilitly to monitor the composition of specific gasses in a vacuum vessel, but also controls the composition of the gasses.

The assembly is shown to include a sputtering chamber 42, having within it a sputtering target 44 and a substrate 46. The chamber 42 is connected via the neck 14 to the analyzer assembly 10 so that gas flows freely between the sputtering chamber 42 and the analyzer assembly 10.

A sputtering partial pressure controller 50 has inputs connected to the photomultiplier tubes 40 of the analyzer assembly 10. This controller 50 computes the partial pressures of the two gas species of interest. The controller 50 has outputs connected to a sputtering power supply 52, to the electron beam generating means 20, 22 of the partial pressure analyzer assembly 10, and to a pair of leak valves 54, 56, which are arranged to admit the two species of gas from respective gas supply sources 58 and 60 to the sputtering chamber 42. A capacitance manometer 62 in communication with the sputtering chamber 42 is also coupled to the control 50, and can be employed for calibration purposes. Also shown is a computer bus 64 for connecting the controller 50 to a central processing computer (not shown) so that the entire sputtering process can be automated.

The sputtering chamber 42, like other process vessels, requires a constant flow of the gasses to remove and dilute contaminants, and in the case of reactive sputtering, at least one species of gas is consumed by chemical reaction. Thus, the amount of gas supplied into the chamber 42 to maintain a constant ratio of partial pressures is constantly changing. In this practical arrangement, control of gas partial pressure is achieved by continuously measuring the value for each species in the vessel, comparing the measured value to the desired value and admitting the appropriate amount of the gas, through the leak valve 54 or 56, to the chamber 42. These leak valves 54 and 56 are commonly available, and may be of the electromagnetic, electromechanical or piezoelectric type. Because of their inherent speed, piezoelectric valves are preferred.

The incorporation of the capacitance manometer 62 is useful, but not essential to the operation of the system. The manometer 62 constitutes a species-independent means of true gas pressure measurements. This manometer 62 is not so much a means of measuring the total gas pressure within the vessel, but rather a pressure standard for calibrating the system. With the manometer 62 installed on the chamber 42, it is simple to adjust electrical amplifiers associated with the photomultiplier tubes 40 so that the relationships between the photons produced and collected relative to the respective gasses are established independently. Once these relationships are known for each gas, operation is possible over a wide range of pressures and gas compositions without further need for capacitance manometer readings.

In an actual embodiment in which this invention was practiced, various nitride (TiN) and oxide (TiO$_2$) films were made. In that operation it was considered useful that the power supply employed for powering the sputtering process be controlled. Surprisingly, it was discovered that simple current control was sufficient in either case, as the plasma impedance was maintained to very close tolerances as a result of the above-described partial pressure control. For this reason, current control for a sputtering operation becomes a simplified yet adequate means of power control. Thus, with this invention it is practical either to use a control system to set the power or to manually set the power level when the deposition was about to commence.

It would be straightforward for anyone skilled in computer programming to automate control of other aspects of system operation, or to automate the calibration of the optical partial pressure analysis with the capacitance manometer.

While the invention has been described hereinabove with respect to a preferred embodiment, it should be recognized that the invention is not confined to that embodiment, and many modifications and variations would present themselves to those skilled in the art without departure from the scope and spirit of this invention, as defined in the appended claims.

I claim:

1. A sensor for measuring the relative amount of a specific gas within a vacuum chamber comprising:
   electron beam generating means providing in a given direction a beam of electrons having sufficient energy to excite the atoms and molecules of said gas whereby said atoms and molecules exite photons indicative of said gas,
   means in communication with said chamber for conducting said gas to said electron beam,
   photodetector means for viewing photons emitted by said atoms and molecules, the photodetector means having a predetermined viewing direction from which said photons are received, and including discriminating means for selecting the photons of said wavelength and excluding others, and means for detecting the intensity of the photons of said selected wavelength and converting said intensity to a proportional electric signal; and
   means mounting said photodetector means relative to said electron beam generating means so that the viewing direction of said photodetector means is substantially orthogonal to said electron beam.

2. A sensor as defined in claim 1 wherein said vacuum chamber operates at a pressure no greater than about $200 \times 10^{-3}$ Torr.

3. A sensor as defined in claim 1 wherein said discriminating means includes one or more interference filters.

4. A sensor as defined in claim 1 wherein said discriminating means includes a diffraction grating.

5. A sensor defined in claim 1 wherein said photosensor means include a photomultiplier tube.

6. A sensor as defined in claim 1 wherein said photosensor means include solid-state light-to-electric conversion means.

7. A sensor as defined in claim 1 further comprising at least one additional photosensor means and an associated at least one discriminating means so that a plurality of gasses can be monitored simultaneously.

8. A sensor as defined in claim 1 wherein said discriminating means includes a plurality of filters having wavelength characteristics of respective gasses, and means for automatically changing said filters to analyze different desired gasses.

9. A sensor as defined in claim 1 wherein said means mounting said photosensor means relative to said electron beam is constructed such that said discriminating means substantially abuts the area excited by said electron beam, so as to maximize the quantity of photons collected by the photosensor means.

10. A sensor as defined in claim 1 wherein said electron beam generating means includes a filament heater which produces blackbody radiation, and said mounting means includes means for preventing said blackbody radiation from reaching said photosensor means.

11. A sensor as defined in claim 1 wherein said electron beam generating means includes a cold cathode discharge element that avoids significant blackbody radiation.

* * * * *

UNITED STATES PATENT AND TRADEMARK OFFICE
CERTIFICATE OF CORRECTION

PATENT NO. : 4,692,630
DATED : September 8, 1987
INVENTOR(S) : Carl A. Gogol

It is certified that error appears in the above-identified patent and that said Letters Patent is hereby corrected as shown below:

Column 6, line 42, "molecules exite" should read "molecules emit".

Signed and Sealed this

Seventeenth Day of May, 1988

Attest:

DONALD J. QUIGG

Attesting Officer

Commissioner of Patents and Trademarks